(12) United States Patent
Keller

(10) Patent No.: US 6,334,875 B1
(45) Date of Patent: Jan. 1, 2002

(54) COTYLOID CAVITY PROSTHESIS

(75) Inventor: Arnold Keller, Kayhude (DE)

(73) Assignee: Waldemar Link (GmbH & Co.), Hamburg (DE)

( * ) Notice: Subject to any disclaimer, the term of this patent is extended or adjusted under 35 U.S.C. 154(b) by 0 days.

(21) Appl. No.: 09/647,845
(22) PCT Filed: May 25, 1998
(86) PCT No.: PCT/EP98/03076
§ 371 Date: Oct. 6, 2000
§ 102(e) Date: Oct. 6, 2000
(87) PCT Pub. No.: WO99/60955
PCT Pub. Date: Dec. 2, 1999
(51) Int. Cl.[7] ..................................... A61F 2/32
(52) U.S. Cl. ..................... 623/22.28; 623/22.24
(58) Field of Search ............... 623/22.28, 22.24, 623/22.26

(56) References Cited

U.S. PATENT DOCUMENTS

| 5,133,764 A | 7/1992 | Frederick |
| 5,507,828 A | 4/1996 | Roland |

FOREIGN PATENT DOCUMENTS

| EP | 0 190 093 A | 8/1986 |

*Primary Examiner*—Corrine McDermott
*Assistant Examiner*—Thomas Barrett
(74) *Attorney, Agent, or Firm*—Morrison & Foerster LLP

(57) ABSTRACT

A cotyloid cavity prosthesis consists of an outer shell (1) and a bearing insert (2) held together by a locking device (3). The locking device comprises an elastic lip (6) and an undercut surface (4) interacting with the latter. The dimensions are chosen such that, once mounted, the tip (9) of the lip rests on the undercut surface (4), with bending deformation of the lip (6). In order to accomplish the latter, the undercut surface (4) forms a smaller angle with the center axis of the prosthesis than does the deformation line of the tip (9) of the lip.

7 Claims, 2 Drawing Sheets

COTYLOID CAVITY PROSTHESIS

BACKGROUND OF THE INVENTION

1. Field of the Invention

The invention relates to a cotyloid cavity prosthesis whose bearing insert is held in an outer shell by means of a locking device which comprises an undercut surface on the outer shell and, engaging behind it, an elastic lip projecting obliquely outwards from the bearing insert towards the open side of the prosthesis.

2. Background of the Invention

In known cotyloid cavity prostheses of this type, the bearing insert made of polyethylene is provided with an elastic retention lip which snaps in behind projections of the outer shell (U.S. Pat. No. 5,133,764). To ensure that the bearing insert sits firmly in the outer shell, the aim is to avoid any play between the lip and the undercut surface. However, since manufacturing tolerances have to be taken into consideration, this aim cannot be achieved in practice.

SUMMARY OF THE INVENTION

The invention is a cotyloid cavity prosthesis of the type which allows the insert to be mounted in the shell in a manner free from play, but with tolerance compensation.

According to the invention, once the bearing insert is mounted in the outer shell, the lip of the bearing insert rests with its tip on the undercut surface, and the undercut surface forms with the mounting device, at the contact point between the tip of the lip and the undercut surface, a smaller angle than the tangent on the deformation line of the tip of the lip at the contact point with the undercut surface. The lip of the bearing insert rests with its tip in a self-locking manner on the undercut surface, with bending deformation of the tip.

The deformation line is the curve on which the tip of the lip, upon bending deformation of the lip, moves under the force exerted by the undercut surface on its tip. At the contact point, this curve has the direction in which the tip of the lip held securely by the undercut surface would move further outwards if the undercut surface were not present. The reference direction for the direction of the undercut surface and of the deformation line of the tip of the lip is the direction of mounting of the insert. It is immaterial which reference direction is chosen for the comparison of these two directions. For the sake of simplicity, the center axis of the prosthesis is specified in this application, but it is not decisive how the direction of this center axis is determined in complex prosthesis shapes, since its exact direction is not the issue, as long as it is fixed.

Under the force of the bending deformation of the lip, the tip of the lip exerts in the radial direction, and in particular in the axial direction, an elastic force on the undercut surface, whose reactive force presses the bearing insert further into the outer shell, until it reaches an end position, free from play, on a limit stop member which is formed, for example, by the bottom of the cotyloid cavity. In doing so, the lip preferably interacts with the undercut surface in a self-locking manner. This is to be understood as meaning that the geometric relationships of the interaction of lip and undercut surface are chosen such that, under the effect of a force seeking to release the insert from the outer shell, the lip cannot slide out along the undercut surface once the lip and the undercut surface are elastically pushed together and cannot snap out, but is instead held securely by friction.

To ensure that this state of assembly is obtained in all cases, the dimensions of the undercut surface and of the lip are chosen in such a way that, even with the greatest deviations in tolerance, the lip in all cases finds the undercut surface. This condition is easy to fulfill since the undercut surface can be designed with an axial extent which is greater than all dimensional tolerances arising in this direction. The invention further provides that all areas of the undercut surface which are intended for contact with the tip of the lip have a diameter which is smaller than the unstressed diameter of the tip of the lip.

In known prostheses of similar type, the lip extends away inwards from the open side of the prosthesis (U.S. Pat No. 5,507,828) and presses radially against the outer shell; the lip does not interact with the contact surface in a self-locking manner and can slide outwards and snap out of place under the effect of a force acting axially towards the open side of the prosthesis.

The undercut surface with which the lip of the bearing insert interacts can be part of a projection, for example of a bead, or of a recess, for example a groove, in particular an annular groove. The recess or the projection can be provided along the whole circumference of the bearing insert or only in parts thereof, and the lip can accordingly be designed as an annular lip or consist of several segments which interact, for example like fingers, with projections designed as catches the above description, it has been assumed that the lip is arranged on the bearing insert and the undercut surface is arranged on the cotyloid cavity, but it is also possible, the other way round, for the lip to be provided on the cotyloid cavity and for the undercut surface to be provided on the bearing insert if the material properties so permit.

BRIEF DESCRIPTION OF THE DRAWINGS

The invention is explained in greater detail below with reference to the drawings, which show an advantageous illustrative embodiment of the invention. In the drawings.

DETAILED DESCRIPTION OF THE PREFERRED EMBODIMENTS

The cotyloid cavity prosthesis of this invention includes an outer shell 1 and a bearing insert 2. The outer shell is made, for example, of metal and is configured externally in any desired manner for implantation in the hip bone.

The insert 2 is made of polyethylene or another material suitable as a bearing. Since this forms the lip in the preferred embodiments of this invention, it should be elastically deformable. The internal configuration of the outer shell 1 corresponds to the external configuration of the insert 2 in such a way that the insert is sufficiently supported by the outer shell. In the example shown, they are spherical and lie one on the other in complete surface contact. This contact must be kept as free from play as possible.

Figure 3:
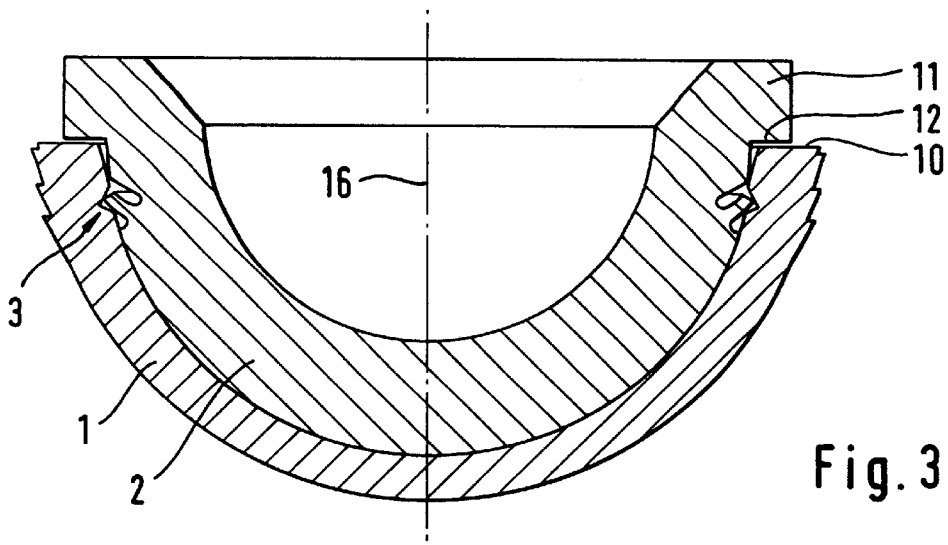
FIG. 3 shows a longitudinal section corresponding to FIG. 1 in the fully mounted state.
Figure 4:
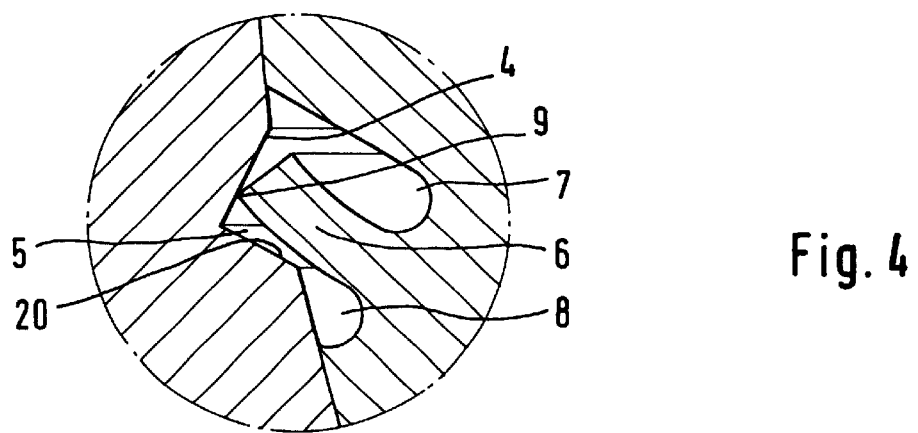
FIG. 4 shows an enlarged partial section of the locking device in the mounted state.
Figure 5:
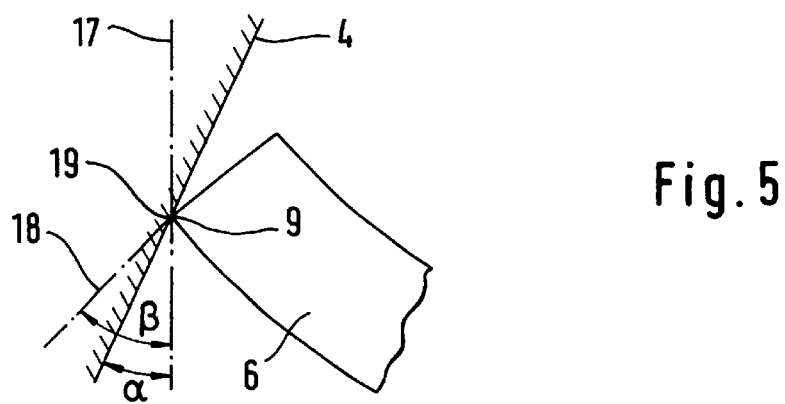
FIG. 5 is a representation of the geometric conditions at the contact point of the lip.

The insert 2 is held in the outer shell 1 by a locking device which is indicated generally by reference number 3 in FIG. 3 and is shown in more detail in FIG. 4. This locking device 3 includes an undercut surface 4 which is formed by a groove 5 in the inner surface of the outer shell, and a lip 6 which projects all round from the insert and interacts with the undercut surface 4. To ensure that the lip 6 has a sufficient length so that it will suitably yield upon engagement with the undercut surface 4, it is surrounded by two grooves 7, 8. It has a tip 9 which is intended to interact with the undercut surface 4. The locking device 3 is arranged near the free edge 10 of the outer shell. The insert 2 has a radially outwardly projecting edge flange 11 which not only serves for strengthening purposes, but also helps the operating surgeon fit the insert into the outer shell 1. Its rear surface 12 interacts, with minimal play, with the front face of the outer shell edge 10 and consequently, at the final stage of the insertion, enforces a position of the insert which comes close to its desired end position and guarantees that the lip 6 engages in the groove 5.

Figure 1:
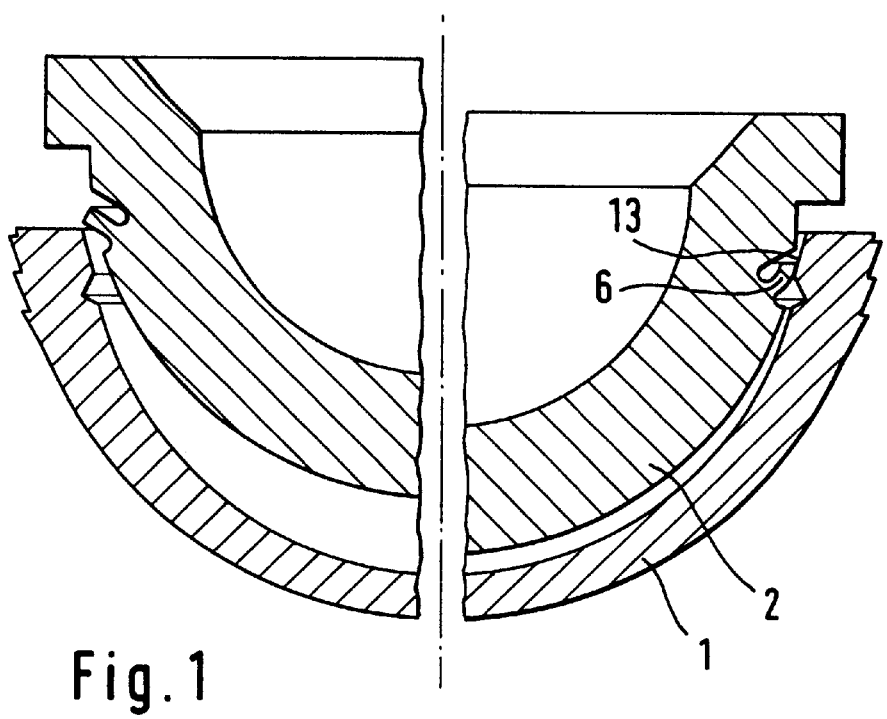
FIG. 1 shows a longitudinal section through a cotyloid cavity in two different phases of fitting.
Figure 2:
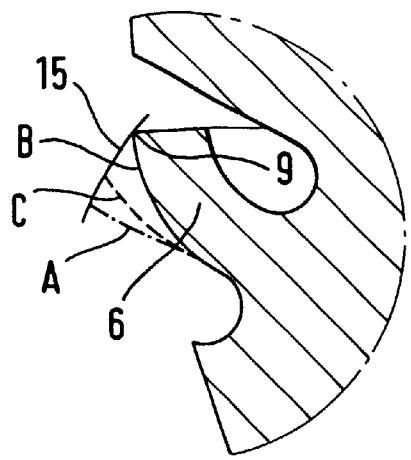
FIG. 2 shows an enlarged partial section illustrating the states of deformation of the lip arising during fitting.

In the unstressed state as originally produced (see left-hand side of FIG. 1), the lip 6 is rectilinear in cross section. It forms overall a cone whose point is directed towards the bottom of the prosthesis. The lip accordingly extends obliquely outwards towards the open side of the prosthesis. In FIG. 2, the outer lip flank in the unstressed, rectilinear state is provided with reference label A.

At the start of the fitting procedure, the lip 6 passes an area 13 which has a considerably smaller diameter than the tip 9 of the lip. The lip is therefore substantially deformed, as is shown on the right-hand side of FIG. 1. This considerably deformed position is indicated in FIG. 2 by reference label B.

As soon as the lip reaches the groove 5, it snaps into it, by springing out radially until it rests on the undercut surface 4, as shown in FIG. 4. This state of bending of the lip is indicated in FIG. 2 by the letter C.

FIG. 2 also shows the line 15 on which the tip 9 of the lip rests in the various states of deformation. In this application, this line is referred to as the deformation line of the tip of the lip. The undercut surface 4 is arranged in such a way that the deformation line 15 impinges on this undercut surface at all times, even in the event of the greatest possible dimensional deviations of the bearing insert and of the outer shell. Moreover, the radius of the undercut surface 4 is chosen in relation to the radius of the tip of the lip in such a way that the part of the undercut surface 4 which can be impacted by the tip of the lip has a smaller diameter than the tip of the lip. It is thus ensured that, once mounted, the tip of the lip at all times rests on the undercut surface 4, with bending deformation of the lip.

In this position, the elastic deformation force of the lip results in a reactive force which seeks to press the bearing insert further into the outer shell. In this way, any areas of play still present are eliminated. This occurs at the latest upon mechanical loading of the bearing insert.

The interaction of the tip 9 of the lip with the undercut surface 4 is ensured if the angle shown in FIG. 4 by the reference $\alpha$, and which the undercut surface 4 forms with a reference line 17 extending parallel to the center axis 16 of the prosthesis, is smaller than the angle $\beta$ between reference line 17 and direction 18, which corresponds to the tangent on the deformation line 15 of the tip of the lip at the contact point 19. This is the direction in which the tip 9 of the lip resting on the undercut surface 4 can move further.

To ensure that the tip of the lip rests on the undercut surface 4, the inner boundary 20 of the groove 5 should always lie at a sufficient distance from the lip 6.

If the angles at which the lip 6 and the undercut surface 4 interact are chosen such that self-locking occurs, or at least if the force under which the lip 6 can slide back on the undercut surface 4 in the mounting direction is greater than the release forces which must be expected when inserting the prosthesis, it can be guaranteed that the insert 2 will be held in the outer shell 1 free from play at all times. For this reason, it is not necessary for the lip 6 to maintain, long-term, the elastic force that still acts immediately after mounting. Instead, when using polyethylene and similar materials, it is to be expected that this force will gradually lessen. However, this does not substantially impair, if at all, the holding action.

The angle $\alpha$ may be between 15° and 40°, more preferably between 20° and 30°. The difference between the angles $\alpha$ and $\beta$ may be not greater than 30° and is advantageously on the order of 20°.

What is claimed is:

1. A cotyloid cavity prosthesis, comprising:

an outer shell and a bearing insert held in the outer shell by means of a locking device which comprises an undercut surface on the outer shell and a locking lip which comprises an elastic tip which engages with bending deformation behind the outer shell and projects obliquely outwardly from the bearing insert toward an open side of the prosthesis, wherein the undercut surface forms an angle $\alpha$ with a center axis of the prosthesis that is smaller than an angle $\beta$ formed between a tangent on a deformation line of the tip of the locking lip at its contact point with the undercut surface, and wherein the tip of the lip, when the bearing insert is fully inserted into the outer shell, rests in a self-locking manner on the undercut surface.

2. A cotyloid cavity prosthesis according to claim 1, wherein the undercut surface comprises a groove.

3. A cotyloid prosthesis according to claim 1, further comprising a limit stop member against which the bearing insert is pressed by a reactive force of the undercut surface against the tip of the locking lip.

4. A cotyloid cavity prosthesis according to claim 1, wherein angle $\alpha$ is between 15° and 40°.

5. A cotyloid cavity prosthesis according to claim 1, wherein angle $\alpha$ is between 20° and 30°.

6. A cotyloid cavity prosthesis according to claim 4, wherein the difference between angles $\alpha$ and $\beta$ is not greater than 30°.

7. A cotyloid cavity prosthesis according to claim 4, wherein the difference between angles $\alpha$ and $\beta$ is about 20°.

* * * * *